United States Patent
Balisky et al.

(10) Patent No.: US 6,899,801 B2
(45) Date of Patent: May 31, 2005

(54) ELECTRODE REFILLING MECHANISM

(75) Inventors: Todd A. Balisky, Corona, CA (US); Srujal (Steven) Patel, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/102,523

(22) Filed: Mar. 20, 2002

(65) Prior Publication Data

US 2003/0178306 A1 Sep. 25, 2003

(51) Int. Cl.[7] .................. G01N 27/403; G01N 27/30
(52) U.S. Cl. ............. 204/435; 204/434; 204/286.1; 204/297.01
(58) Field of Search ............... 204/400, 435, 204/434, 286.1, 297.01

(56) References Cited

U.S. PATENT DOCUMENTS

| | | | |
|---|---|---|---|
| 3,718,567 A | * | 2/1973 | Haddad et al. |
| 3,843,506 A | * | 10/1974 | Jerrold-Jones |
| 4,172,770 A | * | 10/1979 | Semersky et al. |
| 4,273,637 A | * | 6/1981 | MacDonald et al. |
| 4,401,548 A | | 8/1983 | Brezinski ............ 204/435 |
| 4,495,053 A | | 1/1985 | Souza ................ 204/435 |
| 4,686,011 A | | 8/1987 | Jackle ............... 204/1 T |
| 4,714,527 A | * | 12/1987 | Hofmeier et al. |
| 4,770,762 A | | 9/1988 | Schrimm et al. ....... 204/435 |
| 4,891,125 A | | 1/1990 | Schultz ............. 204/435 |
| 5,032,362 A | | 7/1991 | Marsoner et al. ........ 422/81 |
| 5,160,420 A | | 11/1992 | Marsoner et al. ....... 204/433 |
| 5,164,319 A | | 11/1992 | Hafeman et al. ........ 435/291 |
| 5,238,553 A | * | 8/1993 | Hettiarachchi et al. ... 204/435 |
| 5,298,130 A | * | 3/1994 | Ludwig ............ 205/789.5 |
| 5,441,625 A | * | 8/1995 | Ritter et al. |
| 5,445,726 A | | 8/1995 | Cammann ........... 204/153.22 |
| 5,456,811 A | * | 10/1995 | Edwards et al. |
| 5,980,712 A | | 11/1999 | Tauber et al. ......... 204/435 |

* cited by examiner

*Primary Examiner*—Kaj K. Olsen
(74) *Attorney, Agent, or Firm*—Moser, Patterson & Sheridan

(57) ABSTRACT

A method and apparatus for automatically refilling reference electrodes used in chemical analysis. The apparatus generally includes a reference electrode including an outer chamber with an electrolyte contained therein, an adapter to secure the plumbing to the reference electrode, and a computer to control the refill unit. The refill unit further includes a pump, a refill bottle, and plumbing to connect the refill bottle to the pump and the pump to the reference electrode. The method generally includes drawing refill electrolyte from a refill bottle and pumping the refill electrolyte to the reference electrode. Embodiments of the invention further include an automatically refillable reference electrode. The automatically refillable reference electrode generally includes an outer chamber, with an electrolyte contained therein, a reference junction to provide communication between the electrolyte and an electroplating solution, an adapter to secure an electrolyte refill source to a refill opening in the outer chamber, and an overflow hole to drain excess electrolyte from the outer chamber.

7 Claims, 5 Drawing Sheets

ELECTRODE REFILLING MECHANISM

BACKGROUND OF THE INVENTION

1. Field of the Invention

Embodiments of the invention generally relate to a refillable reference electrode used in chemical analysis.

2. Description of the Related Art

Monitoring and/or determining the composition of a plating solution during an electrochemical plating (ECP) process is problematic, as the depletion of certain additives is not generally constant over time, nor is it generally possible to correlate the plating solution composition with the duration of the plating solution use. As such, it is difficult to determine the amount of additives in a plating solution with any degree of accuracy over time, as the level of additives may either decrease or increase during plating, and therefore, the additive concentrations may eventually exceed or fall below a tolerance range for optimal and controllable plating. Conventional ECP systems generally utilize a cyclic voltammetric stripping (CVS) process to determine organic additive concentrations in an ECP solution.

In a CVS process, the potential of a working electrode is generally swept through a voltammetric cycle to estimate an unknown additive concentration. More particularly, three electrodes, a working electrode, a counter electrode, and a reference electrode, are immersed in a cell having plating solution to be measured therein. The reference electrode and the working electrode are typically connected to a device for measuring the electrical potential difference between the respective electrodes. The reference electrode generally consists of three components, a half-cell electrode, a half-cell electrolyte, and a reference junction. As used herein, the term "half-cell electrode" generally refers to a solid phase, electron conducting contact within the half cell electrolyte, at which contact a half-cell oxidation-reduction reaction occurs that establishes a stable potential between the half-cell electrolyte and the working electrode. Direct physical, and therefore electrical, contact between the half-cell electrolyte and the sample plating solution is established through the reference junction, which usually consists of a porous ceramic or metal plug, or other device capable of achieving a fluid mechanical leak. The reference junction is generally necessary to establish electrical contact with the plating solution, and therefore, the working electrode. To prevent contamination of the electrolyte by the plating solution through the reference junction, electrolyte generally leaks from the reference junction into the plating solution. Therefore, the electrolyte solution generally has to be refilled intermittently with liquid electrolyte to maintain a set level of electrolyte in the reference electrode. Conventional reference electrodes generally have an axial hole with a circular cross-section for use as a refill channel, which may be sealed with a plug during analysis.

However, many challenges are associated with refilling conventional reference electrodes. For example, if the electrolyte level falls below a minimum level, the reference electrode will provide unstable results, and therefore, the reference electrode is generally refilled manually, which provides additional problems. Operator errors, such as not promptly refilling the reference electrode, lead to unreliable results. In addition, removing and reinstalling the reference electrode may wear out the electrical contact and may also lead to a noisy response from over tightening the electrode. An approach to eliminate the problem of refilling electrolyte solutions in reference electrodes has been to employ gel filled reference electrodes, which generally do not require refilling. However, gel filled solutions may become contaminated by ion migration into the gel and by depletion from ion migration out of the gel, which results in sensor drift. As such, there is a need for a method and apparatus for refilling reference electrodes, wherein the method and apparatus are not susceptible to the consequences of conventional reference electrode refilling procedures.

SUMMARY OF THE INVENTION

Embodiments of the invention generally provide an electrolyte refill unit for automatically refilling reference electrodes used in chemical analysis. The refill unit generally includes a reference electrode having an outer chamber with an electrolyte contained therein. An adapter is included to secure the plumbing to the reference electrode, and a computer operates to control the refill unit. The refill unit may further include a pump, a refill bottle, and plumbing to connect the refill bottle to the pump and the pump to the reference electrode.

Embodiments of the invention further provide a method for automatically refilling a reference electrode for use in chemical analysis. The method generally includes drawing refill electrolyte from a refill bottle and pumping the refill electrolyte into the reference electrode.

Embodiments of the invention further include a method for automatically refilling a reference electrode for use in chemical analysis. The method generally includes pumping refill electrolyte from an electrolyte refill bottle to an outer chamber of the reference electrode prior to each chemical analysis and draining excess electrolyte from the outer chamber through an overflow hole in the outer chamber.

Embodiments of the invention further include an electrolyte refill unit for automatically refilling reference electrodes used in a chemical analysis of plating solutions. The refill unit generally includes a reference electrode having an outer chamber with an electrolyte immersed therein, a pump, an electrolyte refill bottle, plumbing to connect the electrolyte refill bottle to the pump and the pump to the reference electrode, an adapter having a ferrule to connect a refill opening in the outer chamber of the reference electrode to the plumbing having a cylindrical opening to hold the reference electrode and align the refill opening to the ferrule, an overflow hole, and a computer to control the refill unit.

Embodiments of the invention further include an automatically refillable reference electrode. The automatically refillable reference electrode generally includes an outer chamber, with an electrolyte immersed therein, a reference junction to provide communication between the electrolyte and an electroplating solution, an adapter to secure an electrolyte refill source to a refill opening in the outer chamber, and an overflow hole to drain excess electrolyte from the outer chamber.

BRIEF DESCRIPTION OF THE DRAWINGS

So that the manner in which the above recited features of the present invention are attained can be understood in detail, a more particular description of the invention, briefly summarized above, may be had by reference to the embodiments thereof, which are illustrated in the appended drawings. It is to be noted, however, that the appended drawings illustrate only typical embodiments of this invention, and are therefore, not to be considered limiting of its scope, for the invention may admit to other equally effective embodiments.

DETAILED DESCRIPTION OF THE PREFERRED EMBODIMENTS

Figure 1:
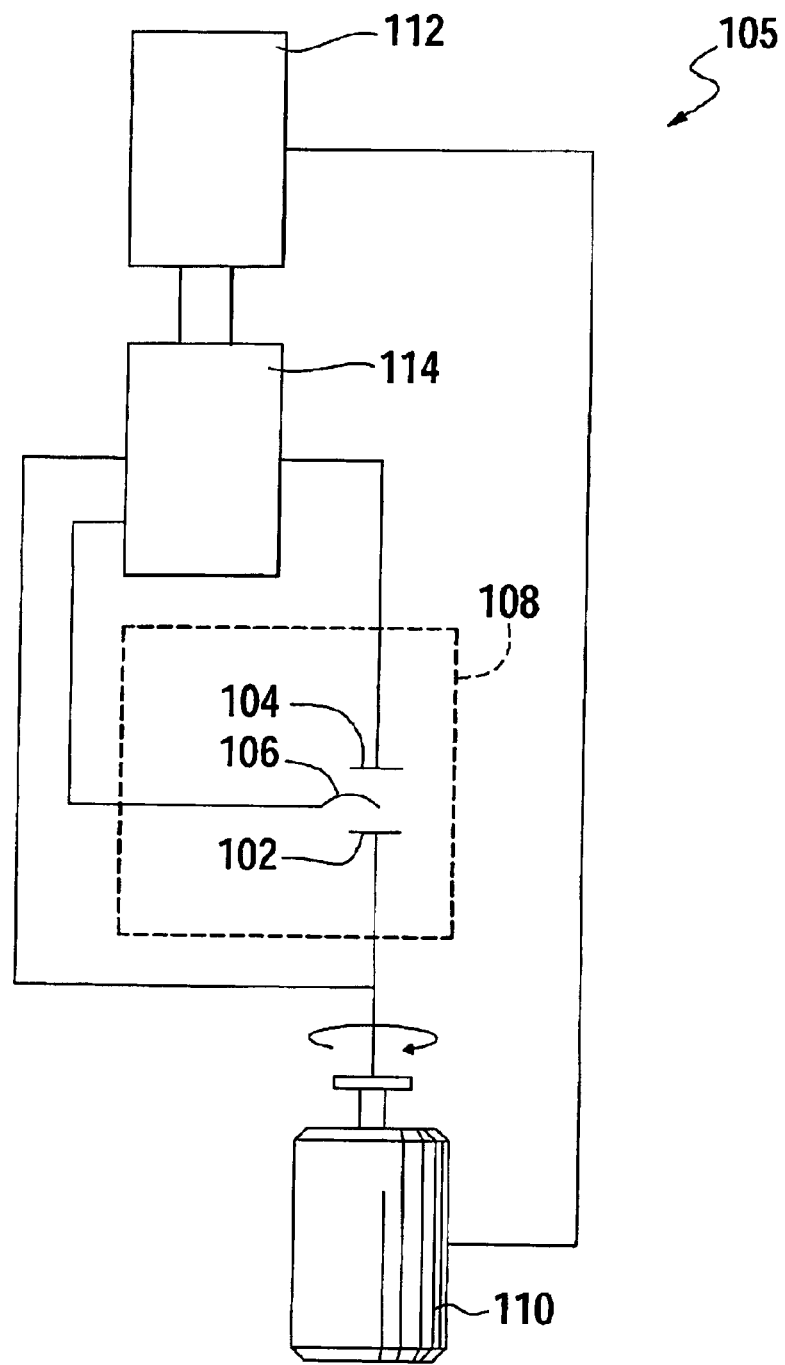
FIG. 1 illustrates a cross-sectional view of a plating solution analysis device.

FIG. 1 illustrates a plating solution analysis device 105 useful in practicing the present invention. Three electrodes, a working electrode 102 of an unknown potential, a current supplying counter electrode 104, and a reference electrode 106 of a known potential, are immersed in a cell 108 having plating solution to be measured therein. The reference electrode 106 may be generally a saturated Calomel reference electrode (SCE) or other metal, such as silver lined with silver chloride or platinum. To establish relative motion between the working electrode 102 and the plating solution, a motor 110 is typically used to rotate the working electrode 102. Without such motion, the plating solution may become depleted at the surface of the working electrode 102 and the deposition rate obtained may not reflect the correct rate for the plating solution. Other means of obtaining relative motion may also be used, such as a pump for moving the plating solution across the face of the working electrode 102.

A computer 112 generally controls an electronic potentiostat 114, which controls the energy input of the working electrode 102 relative to the reference electrode 106. Using a suitable program, the energy input sequences of the present invention may be applied to the working electrode 102. The output of the device 105 can also be plotted on an X-Y recorder to graph each step. The reference electrode 106 establishes a fixed half-cell potential between the plating solution to be measured and the electronic potentiostat 114.

Figure 2:
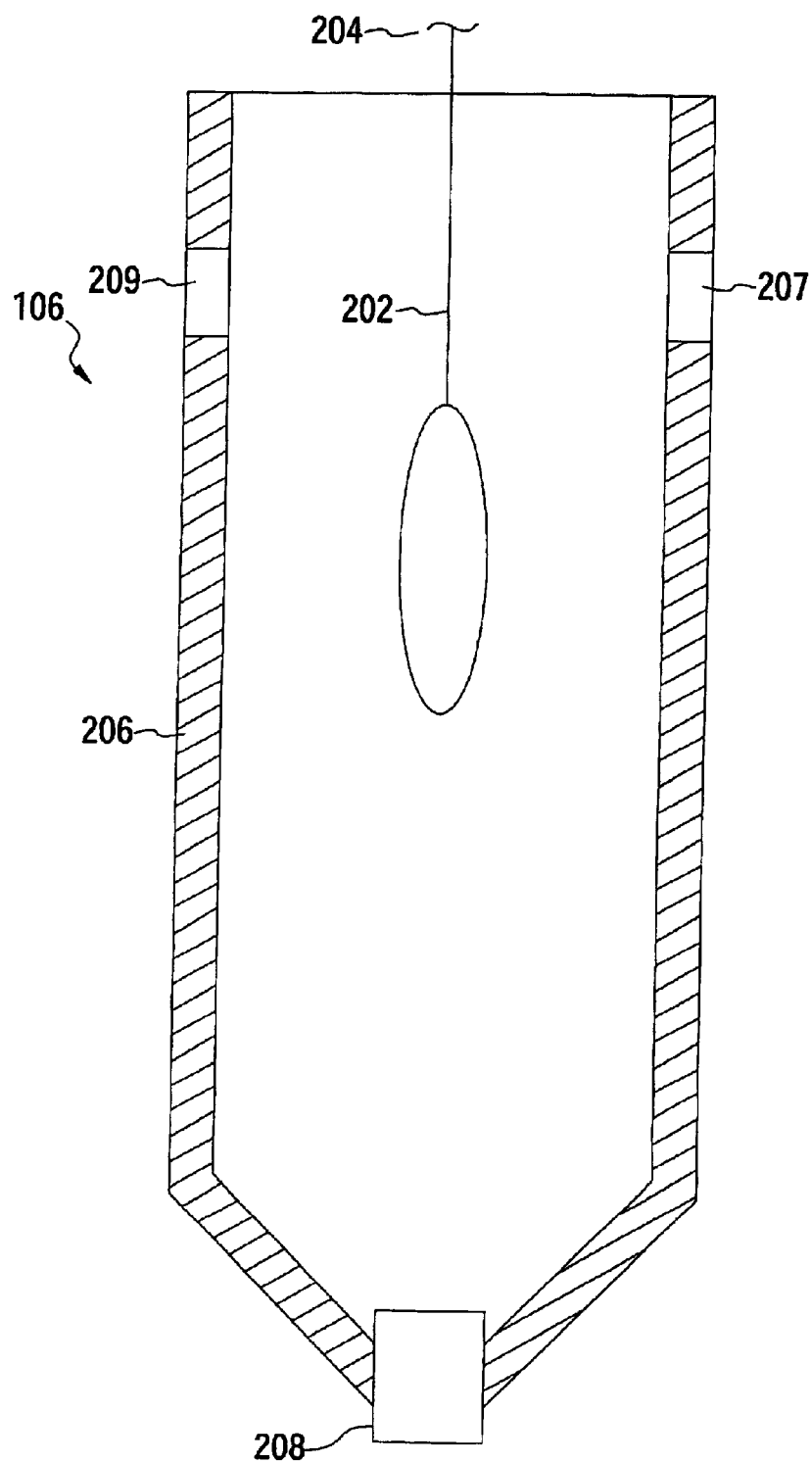
FIG. 2 illustrates a cross-sectional view of a conventional reference electrode.

FIG. 2 illustrates a conventional single junction reference electrode 106 used to make a zero potential electrical reference connection to the plating solution to be tested. The reference electrode 106 generally includes an electrochemical half-cell 202, which may typically be saturated calomel or silver lined with silver chloride, an electrical conductor 204 to make electrical contact with the potentiostat 114 an electrolyte solution, typically liquid potassium chloride saturated with silver chloride or a gel, contained within an outer chamber 206, typically made of glass or plastic and a reference junction 208 through which the electrolyte communicates with the plating solution to be analyzed. The following description of embodiments of the invention will be described by reference to a single junction reference electrode. It is possible, however, to apply embodiments of the invention to other reference electrodes, such as double junction reference electrodes.

In the measurement of unknown solutions, the role of the reference electrode 106 in the chemical analysis is to establish a fixed half-cell potential between the external measured solution and the potentiostat 114. The half-cell 202 should not be directly immersed in the plating solution because its potential would vary with the unknown additive action of the plating solution. Therefore, an indirect reference connection is made by immersing the half-cell 202 into an electrolyte of a known composition, and then establishing physical and electrical contact between the known electrolyte and the plating solution through a reference junction 208. The reference junction 208 may consist of a porous ceramic plug, asbestos fiber, or other means of achieving a fluid mechanical leak. The reference junction 208 functions primarily as a flow restrictor and filtration member, and also serves to define the shape of the interface between the plating solution and the known electrolyte. Ideally, the junction 208 is sufficiently porous to allow a low resistance contact, preferably below 2,000 ohms, between the known electrolyte and plating solution, but is not so porous that the solutions become mutually contaminated. As a result of the fluid leak through the reference junction 208, the electrolyte solution is refilled intermittently to maintain a set level within the outer chamber 206 through a refill opening 207 made in the outer chamber 206 wall. An overflow outlet 209 permits excess electrolyte to discharge and allows the air pressure inside the outer chamber 206 to remain equal to the pressure outside the outer chamber 206, thereby preventing electrolyte from being forced out of the junction 208 into the cell 108.

Figure 3:
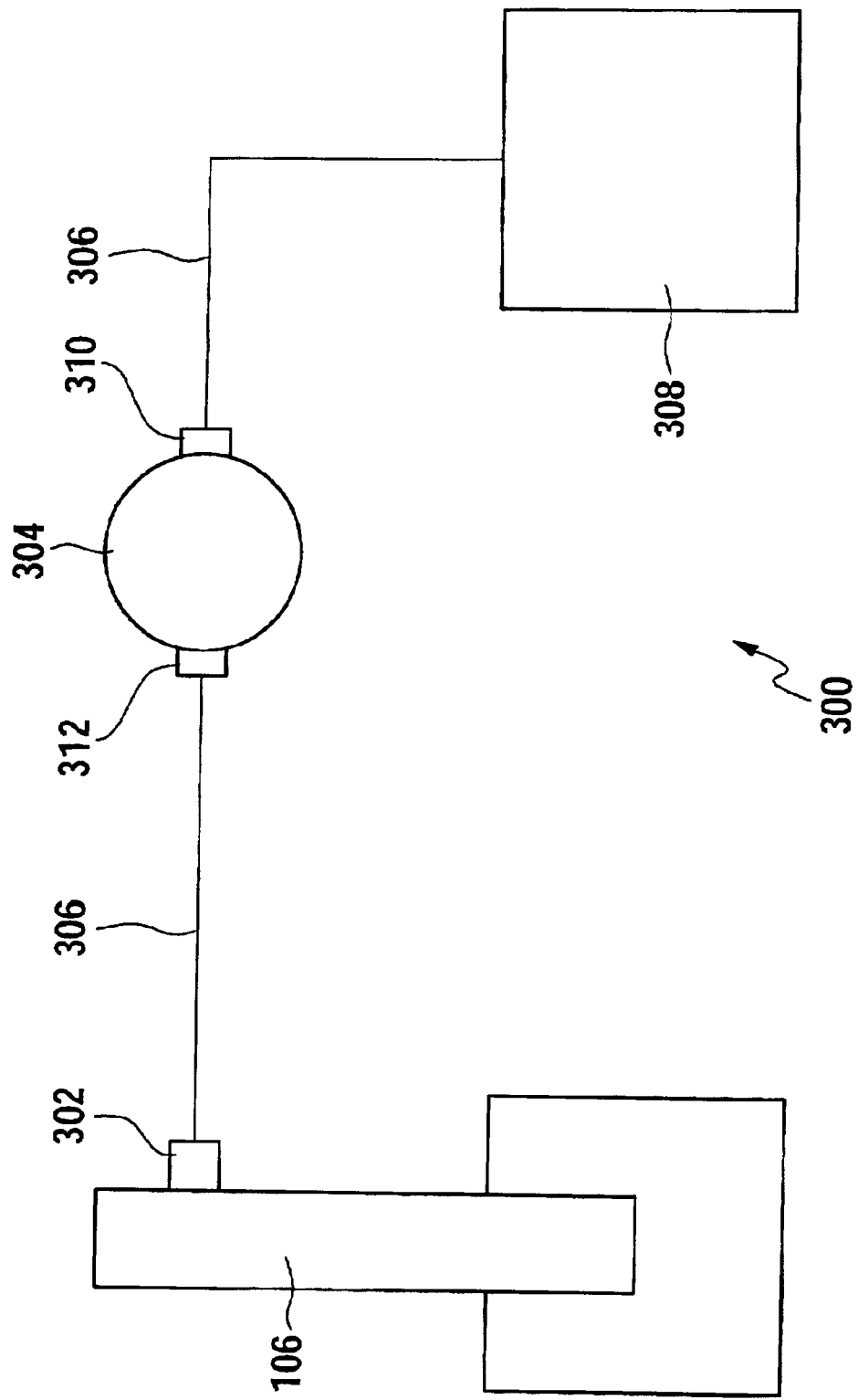
FIG. 3 illustrates a cross-sectional view of an exemplary embodiment of the invention.

FIG. 3 illustrates an exemplary embodiment of the invention including a reference electrode 106 with a refill unit 300. The refill unit 300 includes, an adapter 302, a micropump 304, and plumbing 306 to automatically refill the reference electrode outer chamber 206. The refill unit 300 may be retrofitted to adapt to conventional reference electrodes 106. The micropump 304 draws refill electrolyte from a supply bottle 308 and pumps the electrolyte into the outer chamber 206 of the reference electrode 106 through the adapter 302. The micropump 304 may be under computer control, e.g., software control or a timing device, to automatically refill the electrolyte. Alternatively, the refill unit may include a valve with a pressure supply rather than a pump. The electrolyte may be refilled at any point in time, but exemplary embodiments of the invention contemplate refilling the electrolyte before each analysis of the plating solution. The electrolyte leak rate through the reference junction 108 is generally independent of the analysis frequency, therefore the reference electrode outer chamber 206 may be alternatively refilled only once per day, i.e., in a 24 hour period, in order to conserve electrolyte. The micropump 304 may include any available pump suitable for pumping electrolyte to a reference electrode 106, such as commercially available solenoid micropump, model 090SP24-3 from Bio-chem Valve, Inc., Boonton, N.J. The tubing 306 is connected to the solenoid pump inlet 310 from the refill bottle 308. The electrolyte then passes from the pump outlet 312 to the adapter 302.

The refill unit 300 minimizes operator exposure to corrosive chemicals, daily maintenance to the reference electrode 106, and reference electrode 106 electrolyte level checks. The refill unit 300 also eliminates recovery time necessary after the reference electrode 106 disassembly that was generally associated with manually refilling reference electrodes 106. The limited maintenance required of the refill unit 300 includes an outer solution refill bottle 308 change, which is not frequently necessary. For example, the bottle 308 may be refilled every 40 to 45 days based on a 125 mL bottle 308 and running 16 analyses per day. When the outer chamber 206 is refilled once per day, the bottle 308 may last up to 250 days without a refill bottle 308 change. Alternatively, the bottle 308 may be monitored by a monitoring system to alert an operator when refilling is necessary.

Figure 4:
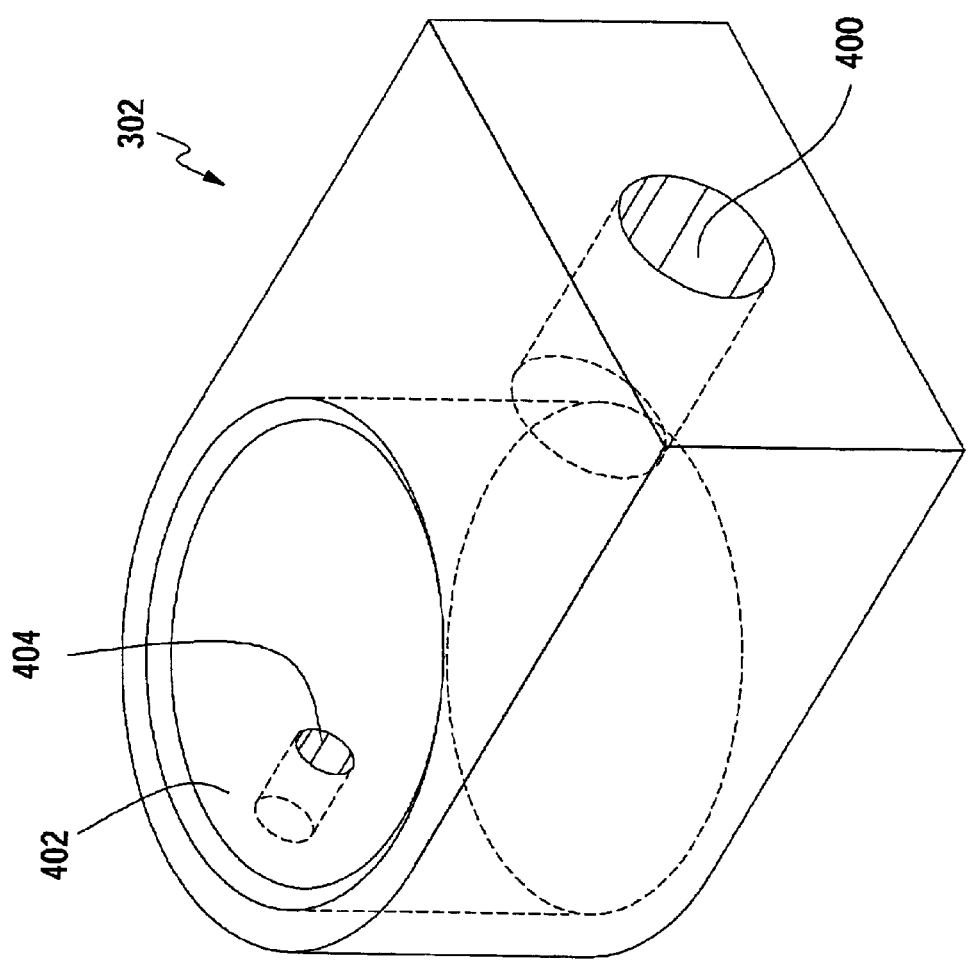
FIG. 4 illustrates an exemplary adapter of the present invention.

FIG. 4 shows an exemplary adapter of the present invention. The adapter 302 is a bracket made of any suitable material, which may include a chemical resin epoxy or other inert, non-conductive material. The adapter 302 includes a ferrule 400, which securely attaches the reference electrode 106 to the plumbing 306 used to pump electrolyte solution to the outer chamber 206 of the reference electrode 106. The ferrule 400 may be any opening in which electrolyte may flow. For example, the ferrule 400 may include a smooth cylindrical opening. The ferrule may alternatively be a threaded hole in which a threaded tube fitting may be screwed. If the ferrule 400 is threaded, the bottom of the hole is generally flat so that plumbing 306 with a flared end may seal against the hole.

The plumbing 306 may include any tubing sufficient for providing a secure connection to the ferrule 400 and transferring electrolyte solution from the refill bottle 308 to the reference electrode 106. The ferrule 400 may correspond to existing refill holes on conventional reference electrodes 106 or may be adapted to any location sufficient to allow electrolyte solution to flow into the outer chamber 206 of the reference electrode 106. The adapter 302 further includes a cylindrical opening 402 to hold the reference electrode 106. The opening 402 is approximately the same diameter as the reference electrode 106 outer chamber 206. The adapter 302 may further include an adapter overflow hole 404. The adapter overflow hole 404 may be positioned opposite the ferrule 400 and may further slope downward, i.e., the portion of the adapter overflow hole 404 on the outside of the adapter 302 is lower than the portion of the adapter overflow hole 404 on the side of the adapter 302 nearest the reference electrode outer chamber 206. Sloping the adapter overflow hole 404 downward allows the electrolyte to be rinsed off of the exterior of the reference electrode outer chamber 206 without introducing rinse solution into the chamber 206. When an overflow hole 209 is not present in the outer chamber 206, an alternative bracket may be used.

Figure 5:
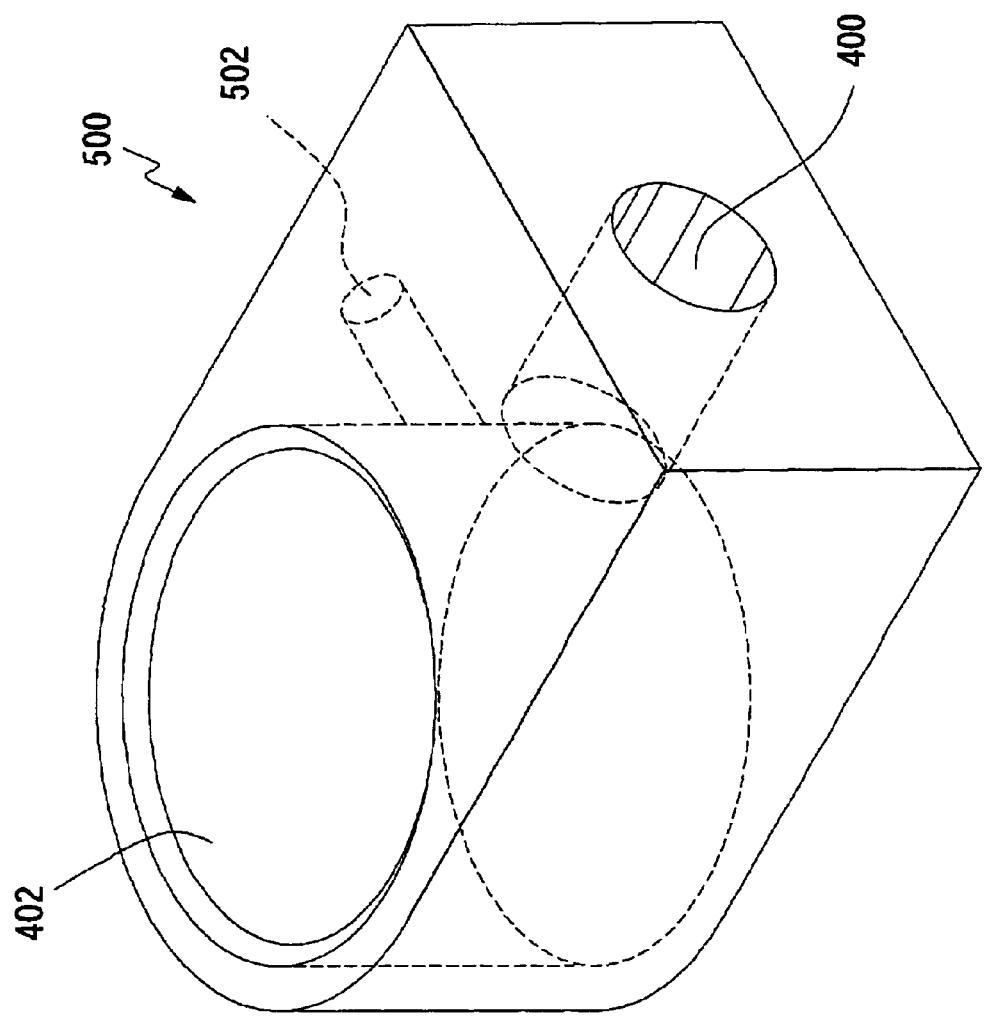
FIG. 5 illustrates an adapter of the present invention.

FIG. 5 illustrates an alternative bracket 500, wherein the ferrule 400 and the adapter overflow hole 502 are adjacent one another. Both the adapter overflow hole 502 and the ferrule 400 may be accommodated by the refill opening 207 in the outer chamber, i.e., the radius of the refill opening is large enough to encompass both the adapter overflow hole 502 and the ferrule 400.

The bracket 302 may be secured to the outer chamber 206 by epoxy cement, or any other means to form a seal between the outer chamber 206 and the bracket 302. For example, two elastomer o-rings may be positioned between the bracket and the outer chamber 206. One of the o-rings would generally be positioned above the refill opening 207 and the other would generally be positioned below the refill opening 207.

While the foregoing is directed to embodiments of the present invention, other and further embodiments of the invention may be devised without departing from the basic scope thereof, and the scope thereof is determined by the claims that follow.

What is claimed is:

1. An electrolyte refill unit for automatically refilling reference electrodes used in chemical analysis, comprising:
   a reference electrode adapted to analyze a plating solution, comprising an outer chamber with an electrolyte contained therein;
   a pump;
   a refill bottle;
   plumbing to connect the refill bottle to the pump and the pump to the reference electrode;
   an adapter, having an adapter overflow hole, to secure the plumbing to the reference electrode; and
   a controller to operate the refill unit, wherein the reference electrode includes an overflow hole aligned with the adapter overflow hole.

2. An automatically refillable reference electrolyte unit for use in chemical analysis, comprising:
   a reference electrode adapted to analyze a plating solution;
   an outer chamber enclosing the reference electrode, the outer chamber being adapted to contain an electrolyte, wherein the outer chamber includes a reference junction adapted to allow a controlled amount of fluid transfer between the electrolyte and a plating solution outside of the chamber;
   a pump in fluid communication with the outer chamber;
   a controller in electrical communication with the pump to control the flow of electrolyte into the outer chamber, wherein the reference electrode has a refill opening and an overflow hole to allow a release of excess electrolyte from the outer chamber upon refilling; and
   a ferrule to provide fluid communication between the pump and the refill opening and an adapter overflow hole aligned with the overflow hole in the reference electrode.

3. A reference electrode unit adapted to facilitate refilling and maintenance, comprising:
   an outer chamber adapted to contain a reference electrolyte and enclosing a reference electrode;
   a reference junction mounted within the wall of the outer chamber, the reference junction providing limited fluid transfer between the reference electrolyte and an electroplating solution outside the chamber, the reference junction minimizing cross contamination between the reference electrolyte and an electroplating solution while providing a low electrical resistance current pathway therebetween; and
   a removable adapter surrounding a portion of the outer chamber and provided with respective fluid passageways for fluid transfer between the outer chamber and a source of refill reference electrolyte, and to permit the release of any excess electrolyte, wherein the removable adapter includes a ferrule aligned with a refill opening in the outer chamber to provide fluid communication with the source of refill reference electrolyte and an adapter overflow hole aligned with an overflow hole in the outer chamber to allow release of excess electrolyte from the outer chamber upon refilling.

4. An adapter securing a reference electrode to facilitate refilling and maintenance of the reference electrode, comprising:
   an outer body securing the reference electrode, the reference electrode having an outer chamber and a refill opening, and the outer body having a ferrule formed in the outer body aligned with the refill opening in the reference electrode to provide refill electrolyte to the outer chamber of the reference electrode, an adapter overflow hole aligned with an overflow hole in the outer chamber formed in the outer body to allow for release of excess electrolyte from the outer chamber upon refilling, and a cylindrical open in the outer body adjacent to the ferrule to hold the reference electrode.

5. The adapter of claim 4, wherein the cylindrical opening has a diameter substantially equal to an outer diameter of the outer chamber.

6. The adapter of claim 4, wherein the adapter is formed of a non-conductive material.

7. The adapter of claim 4, wherein the adapter overflow hole is located adjacent the ferrule and aligned with the refill opening in the outer chamber.

* * * * *